(12) United States Patent
Sugiura

(10) Patent No.: US 10,370,631 B2
(45) Date of Patent: Aug. 6, 2019

(54) CELL CULTURE PACKAGE AND PACKAGE CONTAINING CELL-CULTURE MATERIAL

(71) Applicant: JAPAN TISSUE ENGINEERING CO, LTD., Gamagori-shi, Aichi (JP)

(72) Inventor: Makoto Sugiura, Gifu (JP)

(73) Assignee: JAPAN TISSUE ENGINEERING CO., LTD., Gamigori-shi (JP)

( * ) Notice: Subject to any disclaimer, the term of this patent is extended or adjusted under 35 U.S.C. 154(b) by 160 days.

(21) Appl. No.: 14/914,096

(22) PCT Filed: Nov. 6, 2014

(86) PCT No.: PCT/JP2014/079446
§ 371 (c)(1),
(2) Date: Feb. 24, 2016

(87) PCT Pub. No.: WO2015/076115
PCT Pub. Date: May 28, 2015

(65) Prior Publication Data
US 2016/0208207 A1 Jul. 21, 2016

(30) Foreign Application Priority Data
Nov. 22, 2013 (JP) .................. 2013-241854

(51) Int. Cl.
*C12M 1/00* (2006.01)
*C12M 1/22* (2006.01)
*C12M 1/26* (2006.01)

(52) U.S. Cl.
CPC ............ *C12M 23/14* (2013.01); *C12M 23/34* (2013.01); *C12M 23/38* (2013.01); *C12M 23/58* (2013.01); *C12M 33/04* (2013.01); *C12M 23/10* (2013.01)

(58) Field of Classification Search
CPC ...... C12M 23/14; C12M 23/38; C12M 23/58; C12M 33/04
See application file for complete search history.

(56) References Cited

U.S. PATENT DOCUMENTS 4,603,538 A 8/1986 Shave
5,057,429 A * 10/1991 Watanabe ............. B01F 9/0001
206/213.1

(Continued)

FOREIGN PATENT DOCUMENTS

EP 0258795 A2 3/1988
JP S61-172560 A 8/1986

(Continued)

OTHER PUBLICATIONS

May 24, 2016 International Preliminary Report on Patentability of the International Patent Searching Authority issued in International Application No. PCT/JP2014/079446.

(Continued)

*Primary Examiner* — Gautam Prakash
*Assistant Examiner* — Lydia Edwards
(74) *Attorney, Agent, or Firm* — Oliff PLC

(57) ABSTRACT

An inner bag of a cell culture package is enclosed in an outer bag such that a rubber stopper is exposed to the outside. A closed space surrounded by the outer surface of the inner bag and the inner surface of the outer bag is sterile. This allows the outer surface of the inner bag, which is used for containing cell-containing deformable materials, to be maintained in a sterile condition. Since the cell culture package can be sterilized before a cell-containing deformable material is placed therein, the sterilization conditions can be relatively easily determined without considering the influence on the cell-containing deformable material. In addition, a holder allows liquid to pass through the bottom surface and side surface of a recess and the bottom surface and the side surface of a cover.

8 Claims, 4 Drawing Sheets

(56) References Cited

U.S. PATENT DOCUMENTS

| | | | |
|---|---|---|---|
| 5,935,847 A | 8/1999 | Smith et al. | |
| 6,312,742 B1 | 11/2001 | Wood et al. | |
| 2012/0109144 A1* | 5/2012 | Chin | A61B 17/00 606/114 |

FOREIGN PATENT DOCUMENTS

| | | |
|---|---|---|
| JP | H04-18273 A | 1/1992 |
| JP | 2005-087029 A | 4/2005 |
| JP | 2008-239168 A | 10/2008 |
| JP | 2011-121617 A | 6/2011 |
| WO | 2011/142670 A1 | 11/2011 |
| WO | 2013/175956 A1 | 11/2013 |
| WO | 2013/179913 A1 | 12/2013 |

OTHER PUBLICATIONS

Jun. 29, 2017 Extended Search Report issued in European Patent Application No. 14864638.3.

Sugawara et al., "Current Situation and Future Perspective of Industrialization of Cultured Cartilage—Expectation for Biotechnology-," Biotechnology, 2005, vol. 83, No. 9, pp. 439-441.

Feb. 3, 2015 International Search Report issued in International Patent Application No. PCT/JP2014/079446.

* cited by examiner

US 10,370,631 B2

CELL CULTURE PACKAGE AND PACKAGE CONTAINING CELL-CULTURE MATERIAL

TECHNICAL FIELD

The present invention relates to cell culture packages and packages containing cell-culture material.

BACKGROUND ART

There are known cell culture packages for culturing and containing cell-containing materials such as pieces of tissue and cell suspensions. For example, PTL 1 discloses a cell culture package having a bag-shaped chamber, an opening/closing part that is opened and closed for the inserting and taking out a piece of tissue into and from the chamber, and a tissue holder for holding the piece of tissue in the chamber.

CITATION LIST

Patent Literature

PTL 1: JP 2005-87029 A

SUMMARY OF INVENTION

Technical Problem

In sterilization and other procedures for medical devices, sterility assurance level (SAL) is used as a measure of the probability of any microorganism being present on a medical device after sterilization, and an SAL of $10^{-6}$ or less ensures its sterility. In medical institutions, sterilized medical devices are handled as being clean, whereas unsterilized medical devices are handled as being unclean.

A cell-containing material is placed in the chamber of the package for cell-containing material (culture device) in PTL 1 to obtain a package containing cell-containing material. The cell-containing material, serving as an end product, cannot be sterilized; therefore, its sterility should be ensured in processes such as manufacture and shipment inspection. However, the sterility of the outer surface of the package containing cell-containing material cannot be ensured since it is exposed to the outside. The sterility of packages containing medicines and medical devices can be ensured since they can generally be subjected to sterilization processes such as radiation sterilization and gas sterilization together with the end products contained therein.

Unlike packages containing medicines and medical devices, packages containing cell-containing material containing cell-containing materials, which cannot be subjected to final sterilization, require only the outer surfaces thereof to be sterilized. This needs to be performed by taking into account the risk of damage to the cell-containing materials. Even if only the outer surfaces of the packages could be sterilized, it would be laborious and burdensome to determine the conditions therefor. Even if conditions where the cell-containing materials are not damaged could be determined, sterilization aught be insufficient. Thus, sufficient sterility of the outer surfaces of packages containing cell-containing material cannot be ensured, and they are handled as being unclean in medical institutions. There remains, however, a need for such packages to be handled as being clean. The conditions for the sterilization of packages containing cell-containing materials are also complicated and difficult to determine since even slight variations in processing conditions can affect the cell-containing materials. With the package for cell-containing material in PTL 1, which is intended to hold a piece of tissue, it is also difficult to maintain a cell-containing deformable material (e.g., a cell-containing sol or cell-containing gel), which is readily deformable by external force (in PTL 1, by the pressing force applied by holding), in the desired shape. This package is therefore not suitable for obtaining three-dimensional cell cultures. The package for cell-containing material in PTL 1, in which a cell-containing material is cultured on a culture sheet, also has a problem in that cells do not grow well in the portion in contact with the culture sheet due to an insufficient supply of nutrients from the medium.

In view of the foregoing problems, an object of the present invention, is to maintain the outer surface of a bag for culturing or containing a cell-containing deformable material in a sterile condition. Another object of the invention is to facilitate the determination of sterilization conditions for sterilizing the outer surface of the bag. Still another object of the invention is to allow the preparation of a cell culture material having the desired three-dimensional structure and to provide a cell culture material in which cells are grown by substantially uniformly supplying nutrients over the entire cell-containing deformable material.

Solution to Problem

A cell culture package according to the present invention is a package for containing a cell-containing deformable material. The cell culture package includes:

- an inner bag having a closed inner space;
- a seal disposed on the inner bag;
- a holder disposed in the inner bag and configured to allow liquid to pass at least partially therethrough; and
- an outer bag having a sterilized closed inner space in which the inner bag is enclosed such that the seal is exposed.

The inner bag of the cell culture package is enclosed in the outer bag such that the seal is exposed. The space surrounded by the outer surface of the inner bag and the inner surface of the outer bag is a sterilized closed space. To sterilize this space, the cell culture package may be subjected to sterilization processes such as gamma irradiation before the injection of a cell-containing deformable material. This space, which is closed, is maintained in a sterile condition; therefore, the outer surface of the inner bag, which is used for containing cell-containing deferrable materials, is also maintained in a sterile condition. Since the cell culture package is sterilized before the injection of a cell-containing deferrable material, the sterilization conditions can be relatively easily determined without considering the influence on the cell-containing deformable material. In addition, the holder allows liquid to pass at least partially therethrough. After a cell-containing deformable material is held in the holder, a medium is added to the inner bag. During the culturing of the cell-containing deformable material, nutrients are supplied over the entire cell-containing deformable material so that cells grow substantially evenly. To inject a cell-containing deformable material into the holder, the seal may be detached and then attached after the injection of the cell-containing deformable material. Alternatively, without detaching the seal, the cell-containing deformable material may be injected from a package containing the cell-containing deformable material through the seal into the holder.

The term "cell-containing deformable material" refers to materials that contain ceils and that are readily deformable by external force, including cell-containing sols and cell-containing gels. Examples of cell-containing sols include cell-collagen mixtures prepared from cell suspensions and collagen solutions. The term "cell culture material" refers to cultured tissues obtained by culturing cell-containing deformable materials (particularly, cell-containing gels). The term "seal" encompasses rubber stoppers, described later, and detachable members such as caps and plugs. The seal may optionally contain antimicrobial agents.

In the cell culture package according to the present invention, the seal may be a rubber stopper, the holder may have a recess configured to allow liquid to pass at least in a bottom surface thereof, and the cell-containing deformable material may be injected into the holder by inserting a needle of a syringe containing the cell-containing deformable material into the rubber stopper and injecting the cell-containing deformable material through the needle into the recess. For this type of cell culture package, a needle of a syringe containing the cell-containing deformable material is inserted into the rubber stopper, and the cell-containing deformable material is injected through the needle into the recess of the holder. The rubber stopper may be any rubber stopper that allows a needle of a syringe to be inserted into and removed from the rubber stopper and that has sufficient elasticity to maintain airtightness during the insertion and removal of the needle.

In the cell culture package according to the present invention, the recess may also allow liquid to pass through a side surface thereof. This allows a medium to be supplied to the cells present in the cell-containing deformable material not only from the bottom surface of the recess, but also from the side surface of the recess. After the cell-containing deformable material is held in the recess, a medium is added to the inner bag. During the culturing of the cell-containing deformable material, cells grow more evenly over the entire cell-containing deformable material.

In the cell culture package according to the present invention, the holder may have a cover covering the recess, and the cover may allow liquid to pass therethrough. This reduces the possibility of deformation of the cell-containing deformable material supplied to the holding space surrounded by the recess and the cover. Since the cover allows liquid to pass therethrough, a medium is also supplied through the cover to the holding space.

The cell culture package according to the present invention may further include a frame disposed in the inner bag, and the holder may be detachably secured to the frame. This limits the movement of the holder in the inner bag. Since the holder can be detached from the frame, it can be easily taken out from the inner bag. The frame may be disposed along the edge of the inner bag. For example, if the inner bag is rectangular, the frame may be linear along one side, may be L-shaped along two sides, may be U-shaped along three sides, or may be rectangular along four sides.

In the cell culture package according to the present invention, a plurality of seals may be disposed on the inner bag, a plurality of holders corresponding to the seals may be disposed in the inner bag, and the inner bag may be enclosed in the outer bag such that all seals are exposed. The holders allow a plurality of ceil culture materials to be grown in the same environment, which results in a higher level of equivalence. For example, one of these cell culture materials may be used for inspection, whereas the other cell culture materials may be used for transplantation.

In the cell culture package according to the present invention, the inner bag may have an opening having the seal rubber stopper disposed therein and sealed together with the seal, the outer bag may be closed along an outer edge except for a portion in contact with an outer surface of the opening of the inner bag, and the outer surface of the opening of the inner bag and an inner surface of the outer bag in contact with the outer surface of the inner bag are closed by an inter-bag seal having a weaker adhesion than the opening of the inner bag. It is also desirable that the sides other than the opening have a seal strength low enough to be easily stripped by the hand of an operator. Even if the outer surface of the outer bag of the cell culture package becomes unclean during the transportation of a cell culture material after a cell-containing deformable material is injected into the holder and is cultured, the outer bag can be detached from the inner bag in a sterile room after the transportation to expose the inner bag. The inner bag can thus be handled as being clean. The outer bag can be easily detached from the inner bag while maintaining the airtightness of the inner bag since the adhesion of the inter-bag seal, i.e., the adhesion between the inner bag and the outer bag, is weaker than the adhesion of the opening of the inner bag.

A package containing cell-culture material according to the present invention includes any of the cell culture packages described above and a cell culture material held in the holder. This package containing cell-culture material, using the cell culture package described above, provides the same advantages described above. The cell culture material held in the holder may be in any form. For example, the cell culture material may be a gel culture or a rigid solid culture by culturing.

DESCRIPTION OF EMBODIMENTS

Figure 1:
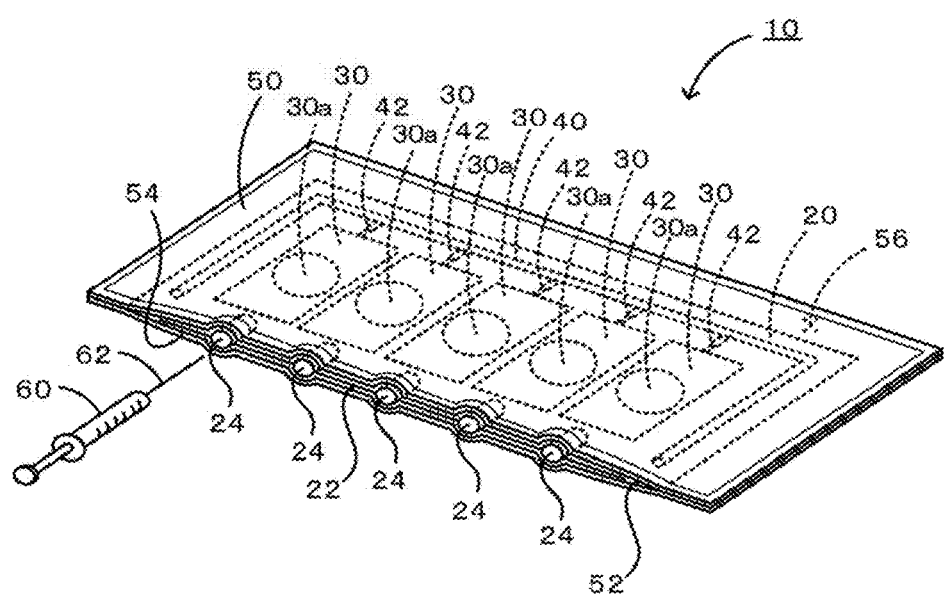
FIG. 1 is a perspective view of a cell culture package 10.
Figure 2:
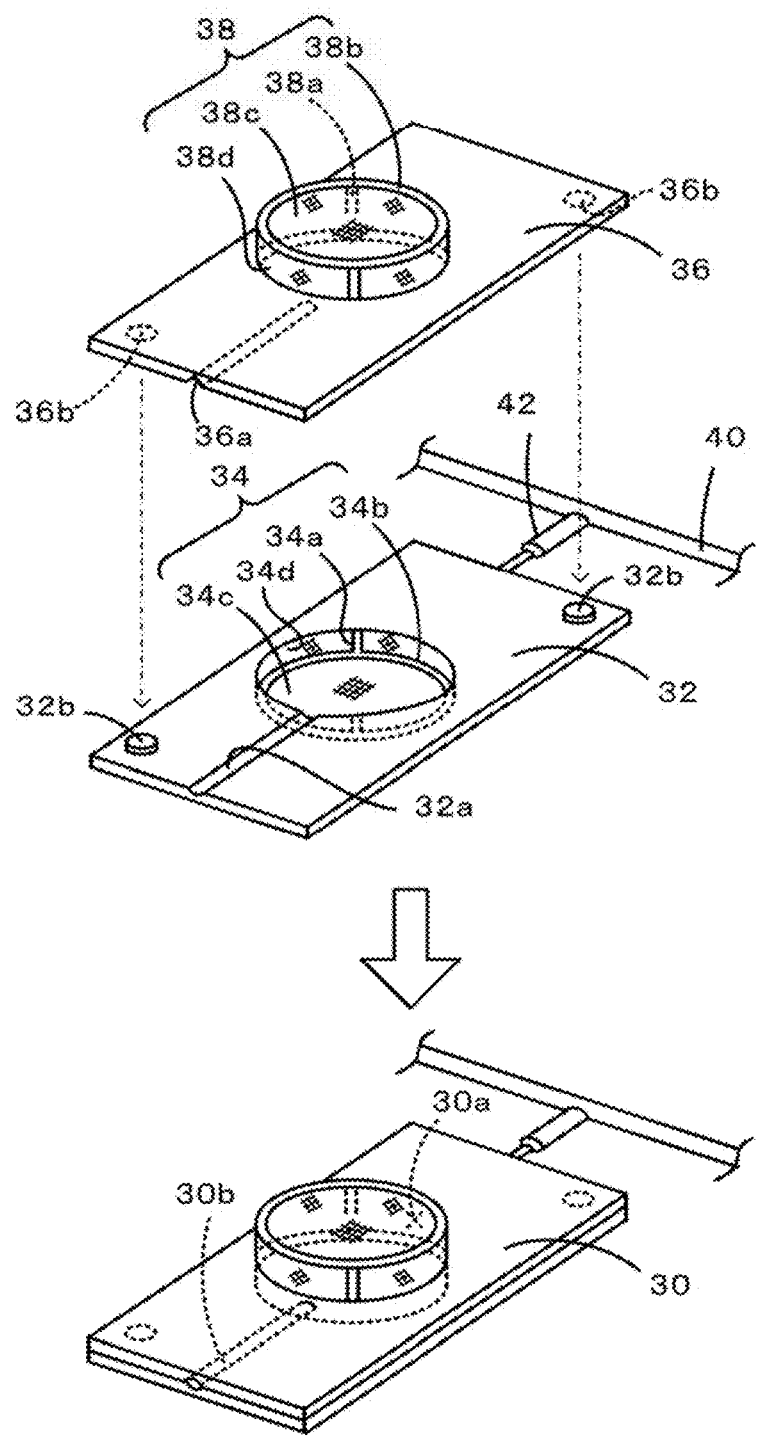
FIG. 2 is a series of perspective views illustrating the assembly of a holder 30.

A preferred embodiment of the present invention will now be described with reference to the drawings. FIG. 1 is a perspective view of a cell culture package 10, and FIG. 2 is a series of perspective views illustrating the assembly of a holder 30.

The cell culture package 10 is a package for containing a cell-containing def erasable material. As shown in FIG. 1, the cell culture package 10 includes an inner bag 20, rubber stoppers 24, holders 30, and an outer bag 50.

The total shape of the inner bag 20 is a generally rectangular bag. The inner bag 20 has an opening 22 having five rubber stoppers 24 disposed therein and sealed by heat welding. A closed space is thus formed in the inner bag 20. Five holders 30 corresponding to the rubber stoppers 24 are disposed in the inner bag 20. A U-shaped resin frame 40 is also disposed in the inner bag 20 along three sides of the inner bag 20. The movement of the frame 40 is thus limited in the inner bag 20.

The rubber stoppers 24 allow a needle 62 of a syringe 60 to be inserted into and removed from the rubber stoppers 24 and have sufficient rubber elasticity to maintain airtightness during the insertion and removal of the needle 62. As used herein, the terra "rubber" refers to known rubbers such as urethane rubber, butyl rubber, ethylene rubber, and silicone rubber as well as other elastomers suited for the intended purpose. These rubbers may be used alone or in a mixture of two or more and may further contain antimicrobial agents.

The holders 30 are secured to the frame 40 with resin branches 42 therebetween. This limits the movement of the holders 30 in the inner bag 20. The branches 42 are thick at the end joined to the frame 40 and are thin at the end joined to the holder 30. To detach the holders 30 from the frame 40, the thin portions of the branches 42 are bent vertically several times until they are broken. As shown in FIG. 2, the holders 30 are each composed of a lower plate 32 having a recess 34 and an upper plate 36 having a cover 38.

The total shape of the lower plate 32 is a rectangular thin resin plate and has a recess 34 extending downward from a circular hole provided around the center thereof. The recess 34 has four thin columns 34a arranged at intervals of about 90° along the outer edge of the circular hole, a thin ring 34b linking the ends of the four columns 34a, a circular bottom surface 34c surrounded by the ring 34b, and side surfaces 34d defined between the outer edge of the circular hole and the ring 34b. A mesh through which liquid can pass is attached to the bottom surface 34c and the side surfaces 34d. The mesh size may be selected so that the cell-containing deformable material used does not leak easily through the mesh. The lower plate 32 has a guide groove 32a extending from the side adjacent to the rubber stopper to the recess 34. The lower plate 32 also has locking protrusions 32b at two diagonal corners of the top surface thereof. The lower plate 32 is secured to the frame 40 with the branches 42 therebetween.

The upper plate 36 is a thin resin plate having the same shape as the lower plate 32 and has a cover 38 covering a circular hole provided around the center thereof. The cover 38 has four thin columns 38a arranged at intervals of about 90° along the outer edge of the circular hole, a thin ring 38b linking the ends of the four columns 38a, a circular top surface 38c surrounded by the ring 38b, and side surfaces 38d defined between the outer edge of the circular hole and the ring 38b. A mesh as described above is attached to the top surface 38c and the side surfaces 38d. The upper plate 36 has a guide groove 36a extending from the side adjacent to the rubber stepper to the cover 38. The upper plate 36 also has locking holes 36b at two diagonal corners of the bottom surface thereof. By fitting the locking protrusions 32b into the locking holes 36b, the upper plate 36 is detachably attached to the lower plate 32 to form the holder 30. A cell-containing deformable material is injected into a holding space 30a surrounded by the recess 34 and the cover 38. The guide grooves 32a and 36a form a guide hole 30b that guides the needle 62 of the syringe 60 into the holding space.

As shown in FIG. 1, the total shape of the outer bag 50 is a rectangular bag closed along the outer edge except for an opening 52. The inner hag 20 is enclosed in the outer bag 50 such that the rubber stoppers 24 of the inner bag 20 are exposed to the outside from the opening 52 of the outer bag 50. The inner surface of the opening 52 of the outer bag 50 is sealed with the outer surface of the opening 22 of the inner bag 20 by heat welding to form an inter-bag seal 54. The inner surface of the opening 52 of the outer bag 50 is sealed with itself by heat welding in the portion where there is no inner bag 20. A closed space 56 is thus formed by the outer surface of the inner bag 20 and the inner surface of the outer bag 50. The closed space 56 is sterilized and is maintained in a sterile condition. The closed space 56 may be sterilized, for example, by irradiation with gamma radiation from the top of the cell culture package 10.

The materials for the inner bag 20 and the outer bag 50 are selected so that the adhesion between the inner surface of the opening 22 of the inner bag 20 and itself after heat welding is stronger than the adhesion between the outer surface of the opening 22 of the inner bag 20 and the inner surface of the opening 52 of the outer bag 50 after heat welding and the adhesion between the inner surface of the opening 52 of the outer bag 50 and itself after heat welding. Examples of resins that can be used for the inner bag 20 and the outer bag 50 include polyvinyl chloride (PVC), polypropylene (PP), polyethylene (PE), ethylene-propylene (EP), ethylene-vinyl acetate (E/VAC), ethylene-vinyl alcohol (E/VAL), polyacrylonitrile (PAN), polystyrene (PS), polymethyl methacrylate (PMMA), polymethyl acrylate (PMA), polyamide (PA), and polyethylene terephthalate (PET). The inner bag 20 and the outer bag 50 are preferably at least made of different materials. For example, the material for the inner bag 20 may be ethylene-vinyl acetate (E/VAC), and the material for the outer bag 50 may be polyethylene (PE). Alternatively, the material for the inner bag 20 may be polyvinyl chloride (PVC), and the material for the outer bag 50 may be polypropylene (PP).

An example where a cell-containing gel is contained and cultured as a cell-containing deformable material in the cell culture package 10 will now foe described with reference to FIG. 1. A cell-containing sol is provided first. The ceil-containing sol may be, for example, a mixture of a chondrocyte suspension and a 3% atelocollagen solution in a predetermined ratio (e.g., 1:4). The chondrocyte suspension may be prepared by adding chondrocytes to 10% FBS-containing DMEM to a predetermined cell density (e.g., $1 \times 10^7$ cells/mL). The resulting cell-containing sol is a highly viscous liquid (slime). The syringe 60 is filled with the cell-containing sol, and the needle 62 is inserted into one of the rubber stoppers 24 of the cell culture package 10. The needle 62 is guided through the guide hole 30b (see FIG. 2) until the tip thereof reaches the holding space 30a (see FIG. 2) surrounded by the recess 34 and the cover 38 of the holder 30. In this state, a predetermined amount of cell-containing sol is injected through the needle 62 into the space 30a by manipulating the piston of the syringe 60. This procedure is repeated for each of the five holding spaces 30a. The cell-containing sol is then left standing in a 5% $CO_2$ atmosphere at 37° C. to cause it to gel. A cell-containing gel in which chondrocytes are embedded is thus held in the holding spaces 30a. A liquid medium is then injected into the inner bag 20 from any rubber stopper 24, and the cell-containing gel is cultured in an incubator. The liquid medium may be, for example, 10% FBS-containing DMEM containing 50 μg/mL ascorbic acid and 100 μg/mL hyaluronic acid. During culturing, the liquid medium is replaced if necessary. The medium is replaced through a needle inserted into any rubber stopper 24.

Figure 3:
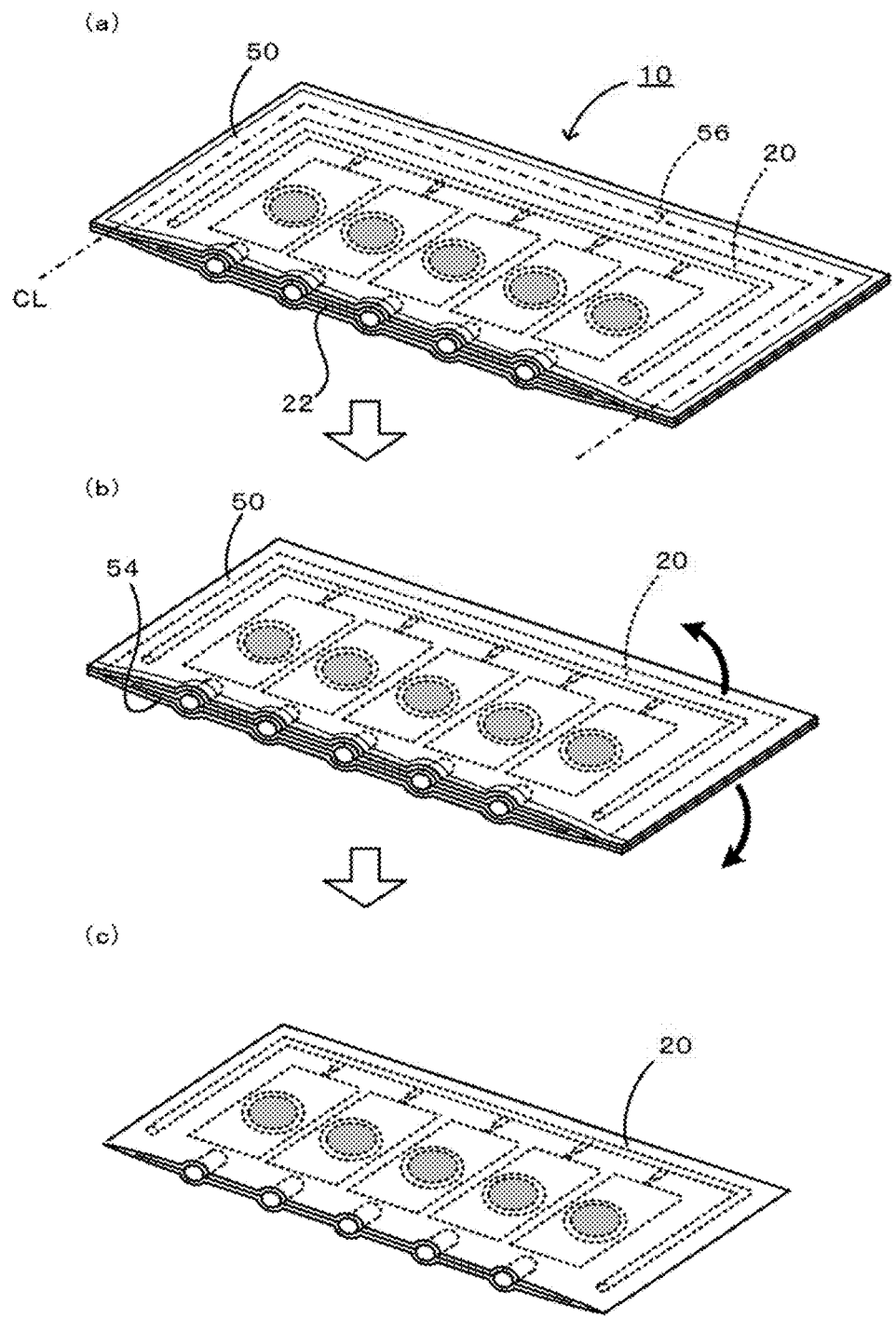
FIG. 3 is an explanatory view of an example where the inner bag 20 is taken out from the cell culture package 10 after the completion of culturing.

An example where the inner bag 20 is taken out from the cell culture package 10 after the completion of culturing will now be described with reference to FIG. 3. In FIG. 3, a cell-containing gel containing cultured chondrocytes is shown in gray. The periphery of the outer bag 50 of the cell culture package 10 is cut along a cut line CL except for the portion in contact with the outer surface of the opening 22 of the inner bag 20 (see FIG. 3(a)). After cutting, the top and bottom surfaces of the outer bag 50 are pinched and are stripped from the inner bag 20 by pulling the top surface upward and the bottom surface downward (see FIG. 3(b)). The adhesion of the inter-bag seal 54 and the adhesion between the outer bag 50 and itself are weaker than the adhesion between the inner bag 20 and itself; therefore, the top and bottom surfaces of the outer bag 50 can be stripped from the inner bag 20 while maintaining the seal between the inner bag 20 and itself. The inner bag 20 is thus taken out (see FIG. 3(c)). The outer surface of the taken out inner bag 20 remains sterile since the closed space 56 between the outer surface of the inner bag 20 and the inner surface of the outer bag 50 had been sterile. The thus-taken out inner bag 20 can be handled as being clean by a clean operator at medical sites. The inner bag 20 is opened by a clean operator and is transferred to a clean area such as a sterilized vat. The cell culture materials containing the chondrocytes are taken out from the inner bag 20 and are used, for example, for transplantation.

As described above, the inner bag 20 of the cell culture package 10 is enclosed in the outer bag 50 such that the rubber stoppers 24 are exposed to the outside. The closed space 56 surrounded by the outer surface of the inner bag 20 and the inner surface of the outer bag 50 is sterile. This allows the outer surface of the inner bag 20, which is used for containing cell-containing deformable materials, to be maintained in a sterile condition. Since the cell culture package 10 can be sterilized before a cell-containing deformable material is placed therein, the sterilization conditions can be relatively easily determined without considering the influence on the cell-containing deformable material. In addition, the holders 30 allow liquid to pass through the bottom surfaces 34c and side surfaces 34d of the recesses 34 and the top surfaces 38c and side surfaces 38d of the covers 38. After a cell-containing deformable material is held in the holding spaces 30a, a liquid medium is added to the inner bag 20. During the culturing of the cell-containing deformable material, cells grow evenly over the entire cell-containing deformable material.

The holders 30 have the covers 38 covering the recesses 34. This reduces the possibility of deformation of the cell-containing deformable material supplied to the holding spaces 30a.

The holders 30 are detachably secured to the frame 40. This limits the movement of the holders 30 in the inner bag 20. Since the holders 30 can be detached from the frame 40, they can be easily taken out from the inner bag 20.

The holders 30 allow a plurality of cell culture materials to be grown in the same environment, which results in a higher level of equivalence. For example, one of these cell culture materials may be used for inspection, whereas the other cell culture materials may toe used for transplantation.

Even if the outer surface of the outer bag 50 of the cell culture package 10 becomes unclean during the transportation of cell culture materials, the outer bag 50 can be detached from the inner bag 20 in a sterile room after the transportation to expose the inner bag 20. The inner bag 20 can thus be handled as being clean. The outer bag 50 can be easily detached from the inner bag 20 while maintaining the airtightness of the inner bag 20 since the adhesion of the inter-bag seal 54, i.e., the adhesion between the outer surface of the opening 22 of the inner bag 20 and the inner surface of the opening 52 of the outer bag 50, is weaker than the adhesion between the inner bag 20 and itself.

It should be appreciated that the foregoing embodiment is not intended to limit the present invention in any way; various embodiments can be made within the technical scope of the present invention.

Figure 4:
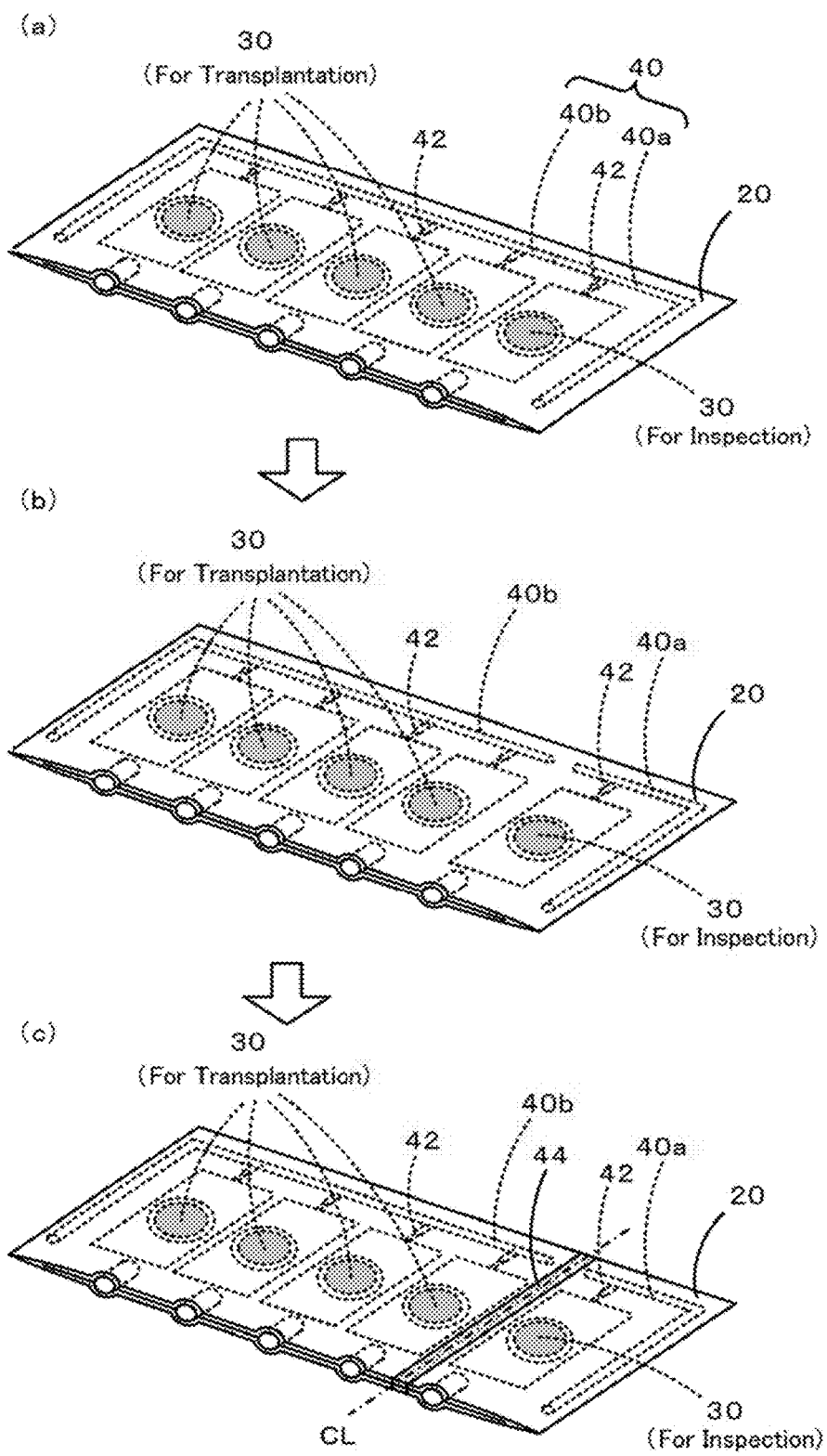
FIG. 4 is an explanatory view of an example of a separable frame 40.

If, in the foregoing embodiment, one of the cell culture materials is used as cells for inspection and the remaining four cell culture materials are used, as cells for transplantation after taking out the inner bag 20, the frame 40 may be separable into a first frame 40a and a second frame 40b, as shown in FIG. 4. For example, a locking hole may be provided at an end of one of the first and second frames 40a and 40b, and a locking protrusion may be provided at an end of the other frame. The two frames 40a and 40b can be joined together by fitting the locking protrusion into the locking hole and can be separated by removing the locking protrusion from the locking hole. The first frame 40a is joined to one holder 30 (at the right end), which holds a cell culture material for inspection, with one branch 42 therebetween, and the second frame 40a is joined to the remaining four holders 30, which hold cell culture materials for transplantation, with the other branches 42 therebetween. The first and second frames 40a and 40b have been joined together before taking out the inner bag 20 from the outer bag 50 (see FIG. 4(a)). An operator then separates the first and second frames 40a and 40b by hand from outside the inner bag 20 (see FIG. 4(b)). A seal 44 is then formed between the holder 30 holding the cell culture material for inspection and the adjacent holder 30 by heat welding using a heat press (see FIG. 4(c)). The frame 40, which has been separated into the first frame 40a and the second frame 40b, does not hinder heat welding. The seal 44 is then cut along a cut line CL extending substantially in the center thereof. The cells for inspection and the cells for transplantation can thus be separated in different bags. Whereas the frame 40 may be separable into two frames, as shown in FIG. 4, it may be separable into three or more frames. For example, the frame 40 may be separable into frames corresponding to the individual holders 30.

Although, in the foregoing embodiment, the holders 30 are composed of the 1 over plate 32 having the recess 34 and the upper plate 36 having the cover 38, the lower plate 32 having the recess 34 may be used alone.

Although, in the foregoing embodiment, both the bottom surface 34c and the side surfaces 34d of the recess 34 are formed by a mesh through which liquid can pass, only the bottom surface 34c may be formed by a mesh. Although both the top surface 38c and the side surfaces 38d of the cover 38 are formed by a mesh through which liquid can pass, only the top surface 38c may be formed by a mesh.

Although the inner bag 20 contains five holders 30 in the foregoing embodiment, it need not necessarily contain five holders 30, but may contain only one holder 30 or two or more holders 30.

Although the holders 30 are substantially disc-shaped in the foregoing embodiment, they may have any desired shape. In this case, the frame corresponding to the columns 34a and ring 34b of each holder 30 may be formed in any suitable shape, and a mesh through which liquid can pass may be attached thereto. In this way, a cell culture having a three-dimensional structure with a complicated shape can be easily prepared in that shape.

Although, in the foregoing embodiment, one of the cell culture materials is used as a cell culture material for inspection and the remaining cell culture materials are used as cell culture materials for transplantation after taking out the inner bag 20, the cell culture material for inspection may be separated by heat pressing from outside the outer bag 50 before taking out the inner bag 20.

Although, in the foregoing embodiment, a liquid medium is supplied to the inner bag 20 through any rubber stepper 24 using a syringe, the liquid medium may instead be supplied, for example, through a pipe extending between the interior of the inner bag 20 and the exterior of the outer bag 50. This allows the liquid medium to flow, thereby constantly supplying a fresh liquid medium, and is also suitable for automation.

Although the rubber stoppers 24 are exposed in the foregoing embodiment, the rubber stoppers 24 may be covered, for example, with aluminum seals. This allows the inlets (rubber stoppers) to be maintained in a clean hygienic condition.

In the foregoing embodiment, a cell-containing gel is placed and cultured in the cell culture package 10 by injecting a cell-containing sol into the recesses 34 of the holders 30 using the syringe 60 and then causing the cell-containing sol to gel to form a cell-containing gel instead of the cell-containing sol, a finely cut cell-containing gel may be injected into the recesses 34 using the syringe 60. This eliminates the need for gelling.

Although the rubber stoppers 24 are used in the foregoing embodiment, they may be replaced by caps or plugs. If caps are used, the caps are detached, and a cell-containing gel (cell-containing deformable material) is injected into the holders 30 using a thin tube, such as a pipette, instead of the syringe 60. After the injection, the caps are attached again to seal the holders 30. This avoids accidents such as piercing with syringe needles, thus improving operator safety. Plugs may also be used in the same manner.

Although the syringe 60 is used in the foregoing embodiment, any package may instead be used that functions as a temporary package for injecting a cell-containing gel (cell-containing deformable material) into the holders 30 and that allows the cell-containing gel to be moved through a needle into the holders 30 by pressing a piston or any other member.

The present application claims priority from Japanese Patent Application No. 2013-241854 filed on Nov. 22, 2013, the entire contents of which are incorporated herein by reference.

INDUSTRIAL APPLICABILITY

The present invention can be used for culturing and containing cell-containing materials such as pieces of tissue and cell suspensions.

REFERENCE SIGNS LIST

10 cell culture package, 20 inner bag, 22 opening, 24 rubber stopper, 30 holder, 30a holding space, 30b guide hole, 32 lower plate, 32a guide groove, 32b locking protrusions, 34 recess, 34a column, 34b ring, 34c bottom surface, 34d side surface, 36 upper plate, 36a guide groove, 36b locking hole, 38 cover, 38a column, 38b ring, 38c top surface, 38d side surface, 40 frame, 40a first frame, 40b second frame, 42 branch, 44 seal, 50 outer bag, 52 opening, 54 inter-bag seal, 56 closed space, 60 syringe, 62 needle.

The invention claimed is:

1. A cell culture package for containing a cell-containing deformable material, including:
   an inner bag having a closed inner space,
   a seal disposed on the inner bag,
   a holder disposed in the inner bag and configured to allow liquid to pass at least partially therethrough, and
   an outer bag having a sterilized closed inner space in which the inner bag is enclosed such that the seal is exposed,
   wherein the holder has a holder-frame formed by columns and a ring in a predetermined three-dimensional shape and a mesh, through which liquid can pass, attached to the holder-frame,
   wherein the columns are arranged in a circumferentially spaced apart relationship, and the ring links an end of each of the columns, and
   wherein the mesh is disposed on side, upper, and lower surfaces of the holder-frame.

2. The cell culture package according to claim 1,
   wherein the seal is a rubber stopper,
   the holder has a recess configured to allow liquid to pass at least in a bottom surface thereof, and
   the cell-containing deformable material is injected into the holder by inserting a needle of a syringe containing the cell-containing deformable material into the rubber stopper and injecting the cell-containing deformable material through the needle into the recess.

3. The cell culture package according to claim 2,
   wherein the recess also allows liquid to pass through a side surface thereof.

4. The cell culture package according to claim 2,
   wherein the holder has a cover covering the recess, and the cover allows liquid to pass therethrough.

5. The cell culture package according to claim 1,
   wherein a frame is disposed in the inner bag, and
   the holder is detachably secured to the frame.

6. The cell culture package according to claim 1,
   wherein a plurality of seals is disposed on the inner bag,
   a plurality of holders corresponding to the seals is disposed in the inner bag, and
   the inner bag is enclosed in the outer bag such that all the seals are exposed.

7. The cell culture package according to claim 1,
   wherein the inner bag has an opening having the seal disposed therein and sealed together with the seal,
   the outer bag is closed along an outer edge except for a portion in contact with an outer surface of the opening of the inner bag, and
   the outer surface of the opening of the inner bag and an inner surface of the outer bag in contact with the outer surface of the inner bag are closed by an inter-bag seal having a weaker adhesion than the opening of the inner bag.

8. A package containing cell-culture material including the cell culture package according to claim 1 and a cell culture material held in the holder.

* * * * *